United States Patent [19]

Black et al.

[11] Patent Number: 4,605,407
[45] Date of Patent: Aug. 12, 1986

[54] HEART VALVE REPLACEMENTS

[75] Inventors: Martin M. Black; Philip J. Drury; Wendy B. Tindale, all of Sheffield, United Kingdom

[73] Assignee: The University of Sheffield, Sheffield, England

[21] Appl. No.: 569,383

[22] Filed: Jan. 9, 1984

[30] Foreign Application Priority Data

Jan. 11, 1983 [GB] United Kingdom ............... 8300636

[51] Int. Cl.⁴ ............................................... A61F 2/24
[52] U.S. Cl. ...................................................... 623/2
[58] Field of Search ................................................ 3/1.5

[56] References Cited

U.S. PATENT DOCUMENTS 3,714,671 2/1973 Edwards et al. .
3,739,402 6/1973 Cooley et al. .
4,470,157 9/1984 Love ..................................... 3/1.5

FOREIGN PATENT DOCUMENTS 1243293 8/1971 United Kingdom .

Primary Examiner—Richard J. Apley
Assistant Examiner—James Prizant
Attorney, Agent, or Firm—King and Schickli

[57] ABSTRACT

A heart valve replacement 12 is characterized by a two-part frame with ring-shaped parts 14, 15 and having cloth coverings 16, 17. At least one leaflet 18 is provided having a margin 18X passing between the two parts 14, 15 of the frame and secured by stitching 19 to the cloth covering 16 of one of the frame parts 14. The frame parts are secured together by stitching 20 between the cloth coverings 16, 17 on the outside of both parts whereby the flexure or hinging line 21 of the leaflet 18 is along the nip between the two cloth-covered frame parts 14, 15. Thus, the line 21 is intermediate the main body of the leaflet 18 and the stitching 19, 20, thereby completely eliminating any possibility of tearing between stitch holes.

4 Claims, 11 Drawing Figures

HEART VALVE REPLACEMENTS

This invention relates to heart valve replacements, and has for its object the provision of a construction avoiding any possibility of flexure or hinging of a flap or leaflet being coincident with or interrupted by a line of sutures or stitches, thus preventing any possibility of tearing between stitch holes.

According to the present invention, a heart valve replacement comprises a two-part frame, with each part generally ring-shaped and covered with cloth, and at least one leaflet having a margin passing between the two parts of the frame and stitched to the cloth covering of one of the frame parts, the frame parts being secured together by stitching between the cloth coverings on the outside of both parts. Thus the flexure or hingeing line of the leaflet will be along the nip between the two cloth-covered frame parts, which line is intermediate the main body of the leaflet and the stitching both of its margin to the cloth-covering of one frame part and of the cloth-covering of both frame parts to each other, completely eliminating any possibility of tearing between stitch holes.

The frame parts are preferably formed of Delrin (registered Trade Mark) and covered with Dacron (registered Trade Mark) cloth.

The frame part to the cloth-covering of which the margin of the leaflet is initially stitched is preferably wire-like in character, so that the margin of the leaflet can be wrapped round it to up to half a turn or more whilst still conforming to the profile of that frame part or part of its profile, which may be flat or convoluted depending on the detailed nature of the heart valve replacement, while the other frame part may be of a wire-like character or may be a portion of a cylinder with a convoluted profile to match a convoluted profile of the frame part to the cloth-covering of which the margin of the leaflet is initially stitched, and the cloth-covering of that other frame part may be united with a cloth-covering of a sewing ring (which ring is preferably formed of P.T.F.E.) before stitching the cloth-coverings of the two frame parts together.

An embodiment of the invention will now be described by way of example only, with reference to the accompanying drawings, in which.

Figure 1:
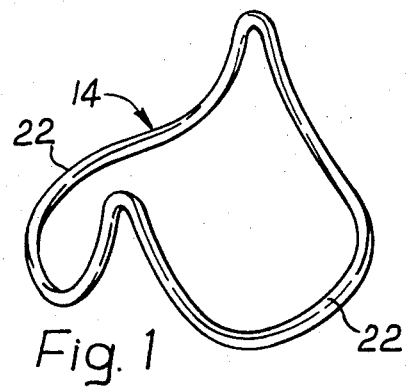
FIG. 1 is an enlarged perspective view of one part (hereinafter called the "female" part) of the two-part frame for a heart valve replacement in accordance with the invention.
Figure 2:
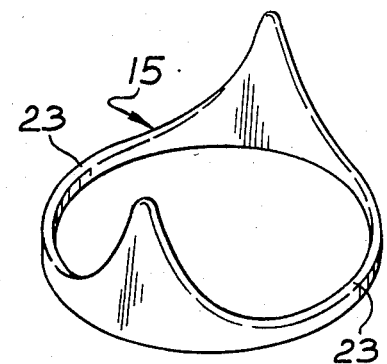
FIG. 2 is a perspective view, to the same scale as FIG. 1, of the other part (hereinafter called the "male" part) of the frame.
Figure 3:
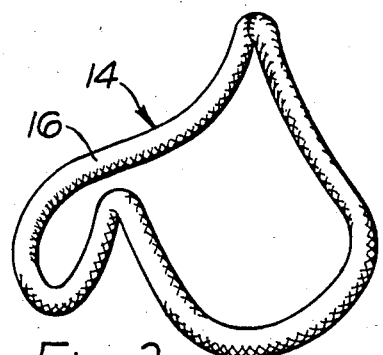
Figure 4:
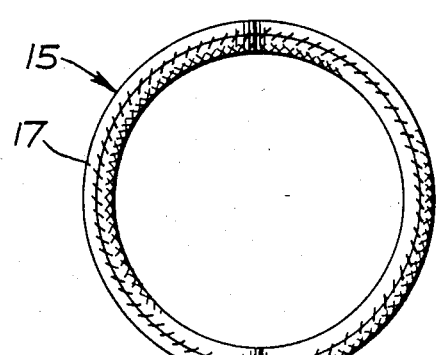
Figure 5:
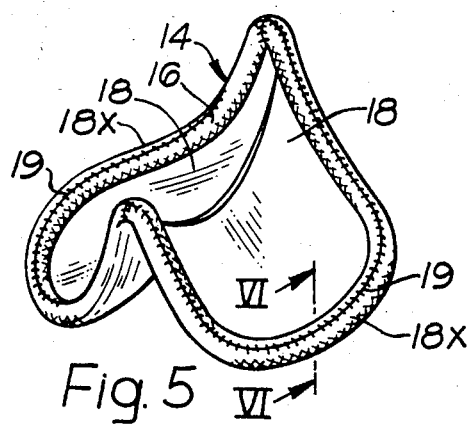
Figure 6:
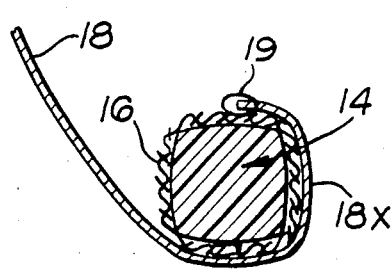
Figure 7:
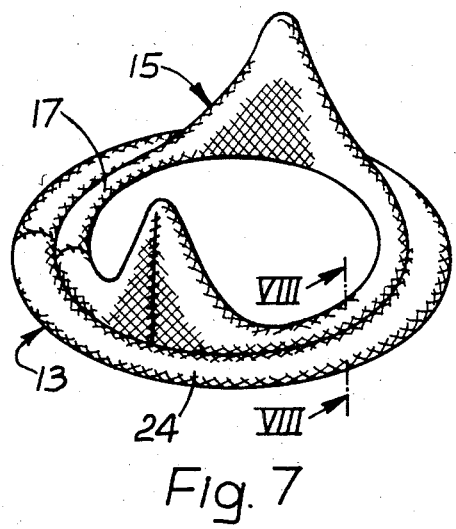
Figure 8:
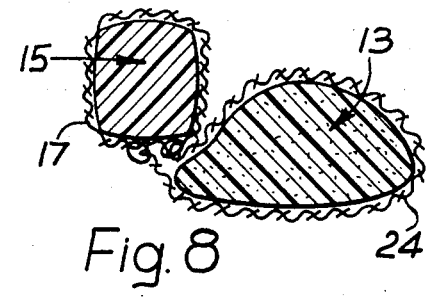
Figure 10:
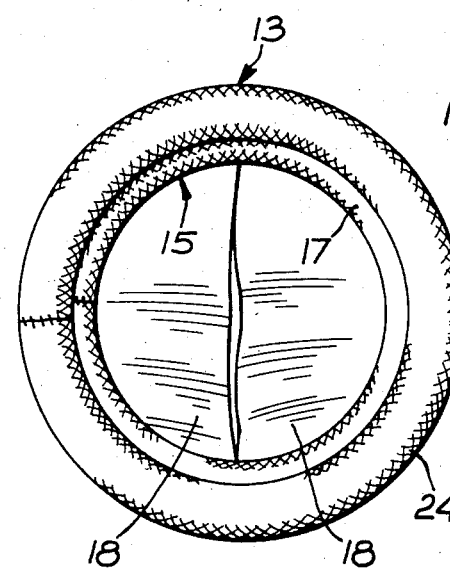
Figure 9:
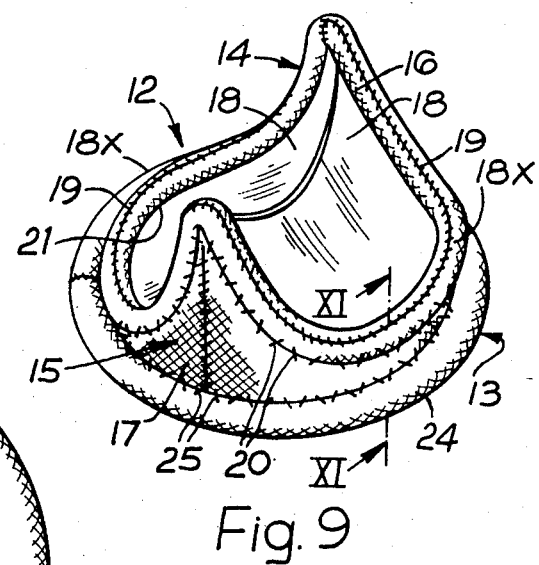
Figure 11:
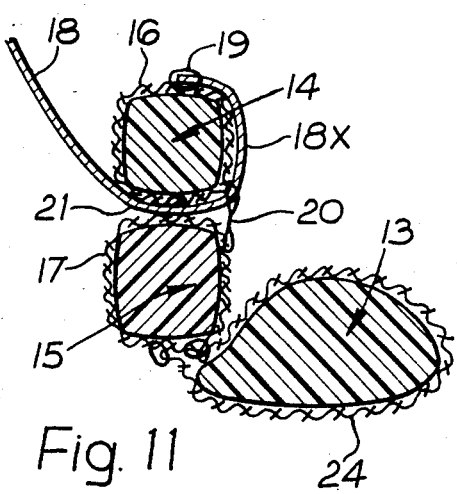

FIG. 3 corresponds to FIG. 1 but shows the female part covered with cloth;

FIG. 4 is an underneath plan of the female part as shown in FIG. 3;

FIG. 5 corresponds to FIG. 3 but shows two leaflets stitched to the cloth covering of the female part;

FIG. 6 is a further enlarged fragmentary section take on the line of VI—VI of FIG. 5;

FIG. 7 corresponds to FIG. 2 but shows the male part covered with cloth, which cloth covering is united with a cloth covering of a sewing ring;

FIG. 8 is a fragmentary section, to the same scale as FIG. 6, taken on the line VIII—VIII of FIG. 7;

FIG. 9 is a perspective view, to the same scale as the preceding perspective views, showing the completed heart valve replacement (together with its sewing ring);

FIG. 10 is an underneath plan of the heart valve replacement as shown in FIG. 9; and FIG. 11 is a fragmentary section, to the same scale as FIGS. 6 and 8, taken on the line XI—XI of FIG. 9.

The heat valve replacement 12 (shown complete with a sewing ring 13 in FIGS. 9 and 10) comprises a two-part frame consisting of a female part 14 (FIG. 1) and a male part 15 (FIG. 2), with each part generally ring-shaped and covered with cloth 16 (FIG. 3) and 17 (FIG. 7) respectively, and a pair of leaflets 18 each having a margin 18X passing between the two parts of the frame (see FIG. 11) and continuing around the outside of the female part 14 to stitching 19 securing it to the cloth-covering 16 of the female part 14, the frame parts 14, 15 being secured together by stitching 20 between the cloth-coverings 16, 17 on the outside of both parts.

Thus the flexure or hingeing line 21 of each leaflet 18 will be along the nip between the cloth-covered frame parts, which line is intermediate the main body of the leaflet and the stitching 19 of its margin 18X to the covering 16 of the female frame part 14 and the stitching 20 of the cloth-coverings 16, 17 of both frame parts 14,15 to each other, completely eliminating any possibility of tearing between stitch holes.

The frame parts 14, 15 are formed of Delrin (registered Trade Mark) and covered with Dacron (registered Trade Mark) cloth 16,17.

The female frame part F (to the cloth-covering 16 of which the margin 18X of each leaflet 18 is initially stitched—see also FIGS. 5 and 6) is wire-like in character, so that the margin 18X of each leaflet 18 can be wrapped round it to half a turn or more whilst still conforming to part 22 the profile of the female frame part, which is convoluted (because the heart valve replacement 12 is a biscuspid mitral valve replacement) and the male frame part 15 is a portion of a cylinder with a convoluted profile 23 to match the profile of the female part.

The cloth-covering 17 of the male frame part 15 is united with a cloth-covering 24 of the sewing ring 13 (which is formed of P.T.F.E.) and—as indicated by FIGS. 7 and 8—before stitching the cloth-coverings 16, 17 of the two frame parts 14,15 together (as shown in FIGS. 9 to 11). Thus the cloth-covering 17 resembles a pair of trousers with the cloth-covering 24 resembling its waistband.

Finally, the cloth-covering CSR of the sewing ring 13 is preferably stitched to the cloth-covering 17 of the male frame part 15 as shown as 25 in FIG. 9, to maintain the general position of the sewing ring relative to the frame parts 14,15 as shown by FIG. 11 without inhibiting the ability of the sewing ring to conform to the respective aperture in a heart.

What we claim is:

1. A heart valve replacement, comprising
   a two-part frame with parts defining a nip therebetween, one part being generally cylindrical, and the other part being generally ring-shaped and wire-like;
   cloth coverings over both frame parts;
   at least two leaflets each having a margin passing between the two frame parts and continuing around the wire-like frame part to a line of stitching spaced from the nip and connecting said leaflet to the cloth covering of that wire-like frame part; and stitching spaced from said nip and between the cloth coverings of the two frames securing said frame parts together;

said nip between the two frame parts defining flexure lines, one along each of said leaflets spaced from the line of stitching between said leaflet and the wire-like frame part and from the stitching securing said two frame parts together, whereby during leaflet flexing tearing of either of said leaflets between stitch holes of the stitching is eliminated.

2. A heart valve replacement as in claim 1, wherein said wire-like frame part is convoluted and the other frame part is a portion of a cylinder with a convoluted profile to match the convoluted profile of said wire-like frame part.

3. A heart valve replacement as in claim 1, further including a cloth covered ring, said sewing ring being connected to said generally cylindrical frame part by the cloth coverings of said sewing ring and said generally cylindrical frame part.

4. A heat valve replacement as in claim 1, wherein said heart valve includes a valve opening and said wire-like frame part is adjacent said opening.

* * * * *